US009545386B2

(12) United States Patent
Forbes et al.

(10) Patent No.: US 9,545,386 B2
(45) Date of Patent: Jan. 17, 2017

(54) METHODS OF TREATING INFECTIOUS DISEASES (71) Applicant: SLIPPERY ROCK UNIVERSITY FOUNDATION, INC., Slippery Rock, PA (US)

(72) Inventors: Wayne M. Forbes, Butler, PA (US); Carolyn S. Steglich, Harrisville, PA (US)

(73) Assignee: SLIPPERY ROCK UNIVERSITY FOUNDATION, INC., Slippery Rock, PA (US)

( * ) Notice: Subject to any disclaimer, the term of this patent is extended or adjusted under 35 U.S.C. 154(b) by 0 days.

(21) Appl. No.: 14/492,368

(22) Filed: Sep. 22, 2014

(65) Prior Publication Data

US 2015/0011649 A1 Jan. 8, 2015

Related U.S. Application Data (62) Division of application No. 13/028,279, filed on Feb. 16, 2011, now Pat. No. 8,865,774, which is a division of application No. 11/839,392, filed on Aug. 15, 2007, now Pat. No. 7,910,114.

(51) Int. Cl.
*A61K 31/11* (2006.01)
*A01N 35/02* (2006.01)
*A61K 36/23* (2006.01)
*A01N 25/34* (2006.01)

(52) U.S. Cl.
CPC ............... *A61K 31/11* (2013.01); *A01N 35/02* (2013.01); *A61K 36/23* (2013.01)

(58) Field of Classification Search
None
See application file for complete search history.

(56) References Cited

U.S. PATENT DOCUMENTS

| | | | | |
|---|---|---|---|---|
| 4,617,394 | A | * | 10/1986 | Blumbergs et al. .......... 546/157 |
| 5,703,236 | A | | 12/1997 | Saksena et al. |
| 5,821,107 | A | | 10/1998 | Carlow et al. |
| 5,863,775 | A | | 1/1999 | Atkinson et al. |
| 7,709,534 | B2 | | 5/2010 | Forbes et al. |
| 7,910,114 | B2 | | 3/2011 | Forbes et al. |
| 8,865,774 | B2 | | 10/2014 | Forbes et al. |
| 2005/0014730 | A1 | | 1/2005 | Carlson et al. |
| 2005/0100561 | A1 | | 5/2005 | Sheen et al. |
| 2007/0160686 | A1 | | 7/2007 | Augustin et al. |
| 2012/0009255 | A1 | | 1/2012 | Forbes et al. |

FOREIGN PATENT DOCUMENTS

JM 3325 9/2002

OTHER PUBLICATIONS van den Hemel et al, Ligand Induced Conformational Changes in the Capping Subdomain of a Bacterial Old Yellow Enzyme Homologue and Conserved Sequence Fingerprints Provide New Insights into Substrate Binding, Journal of Biological Chemistry 2821 (2006) 28152-28161 (Jul. 20, 2006).*
Hill et al. Inhibition of Human Cytochrome P450e1 by Eryngial and Related (2e)-Alkanals and Alkenals, General Poster Session VII, Nov. 13, 2004.*
Perel et al, Non-Communicable Diseases and Injuries in Latin Americ and the Caribbean: Time for Action, PLoS Med 3(9) (Sep. 2006).*
Payne, D. et al., "Antimicrobials the challenge of antibiotic resistant bacterial pathogens: the medical need, the market and prospects for new antimicrobial agents", Current Opinion in Microbiology, 2004, pp. 435-438, vol. 7.
Moellering, Robert C., Jr., et. al., "Antimicrobial Resistance Prevention Initiative—An Update: Proceedings of an Expert Panel on Resistance", The American Journal of Medicine, 2007, pp. S4-S25, vol. 120(7).
Dagar, H. S. et al., "Plant Folk Medicines among the Nicobarese of Katchal Island, India", Economic Botany, 1991, pp. 114-119, vol. 45.
Granzer, Monika et al., "Host-Finding and Host Recognition of Infective Ancylostoma Caninum Larvae", International Journal for Parasitology, 1991, pp. 429-440, vol. 21(4).
Kopp, Steven R. et al., "High-level pyrantel resistance in the hookworm Ancylostoma caninum", Veterinary Parasitology, 2007, pp. 299-304, vol. 143 (3-4).
Tiwari, J. et al., "Detection of benzimidazole resistance in Haemonchus contortus using RFLP-PCR technique", Veterinary Parasitology, 2006, pp. 301-307, vol. 138 (3-4).
Gill, Jennifer H. et al., "Detection of Resistance to Ivermectin in Haemonchus Contortus", International Journal for Parasitology, 1991, pp. 771-776, vol. 21(7).
Vickers, M. et al., "Resistance to macrocyclic lactone anthelmintics by Haemonchus contortus and Ostertagia circumcincta in sheep in New Zealand", New Zealand Veterinary Journal, 2001, pp. 101-105, vol. 49(3).
Kaminsky, R. et al., "In vitro assays to determine drug sensitivities of African trypanosomes: a review", Acta Tropica, 1993, pp. 279-289, vol. 54.
Rifkin, Mary R. et al., "Trypanosome variant surface glycoprotein transfer to target membranes: A model for the pathogenesis of trypanosomiasis", National Academy of Sciences, 1990, pp. 801-805, vol. 87.
Abenga, J. N. et al., "Implicating roles of animal reservoir hosts in the resurgence of *Gambian trypanosomosis* (Sleeping Sickness)", African Journal of Biotechnology, 2005, pp. 134-137, vol. 4(2).
Olila, D. et al., "Bioassay-guided studies on the cytotoxic and in vitro try-panocidal activities of a sesquiterpene—(Muzigadial) derived from a Ugandan medicinal plant (*Warburgia ugandensis*)", African Health Sciences, 2001, pp. 12-15, vol. 1.

(Continued)

Primary Examiner — David J Blanchard
Assistant Examiner — Sarah Chickos
(74) Attorney, Agent, or Firm — Eckert Seamans Cherin & Mellott, LLC; Carol A. Marmo (57) ABSTRACT The present invention provides methods of treating a human or other mammal infected with a parasitic microorganism by administering an effective amount in unit dosage form of a $C_8$-$C_{16}$-alpha, beta-unsaturated aliphatic aldehyde, such as trans-2-dodecenal, to the human or other mammal. The parasitic microorganisms may include trypanosomes, bacteria, fungi and nematodes.

8 Claims, 1 Drawing Sheet

(56) References Cited

OTHER PUBLICATIONS

Hammer et al. (Journal of Applied Microbiology. 1999; 86: 985-990).
Bisignano et al. (FEMS Microbiology Letters. 198: 9-13).
Kubo et al. (Journal of Agricultural and Food Chemistry. 2004; 52: 3329-3332).
Janssen et al. (Pharmaceutisch Weekblad Scientific Edition. 1984; 6: 157-160).
Hill et al. (General Poster Session VII, Saturday, Nov. 13, 2004 from the 56th Southeast Regional Meeting 2004 (Nov. 10-13, 2004).
Delaquis et al International Journal of Food Microbiology. 2002; 74: 101-109.
Eyres et al. Journal of Separation Science. 2005; 28: 1061-1074.
Dorris et al. Molecular Phylogenetic Analysis of the Genus Strongyloides and Related nematodes, International Journal for Parasitology 32 (2002) 1507-1517.
Battinelli et al., "In vitro antifungal and anti-elastase activity of some aliphatic aldehydes from *Olea europaea* L. fruit", Phytomedicine, 13 (2006) 558-563.
Rahman et al., "Antifungal Activities and Essential Oil Constituents of Some Spices from Pakistan", Uploaded to Internet Aug. 29, 1999.
Bueno et al., "Antifungal Sordarins, Synthesis and Structure—Activity Relationships of 3',4'-Fused Dioxolane and Dioxane Derivatives", Bioorganic & Medicinal Chemistry Letters 12 (2007) 121-124.

* cited by examiner

Fig. 1A. Growth of *P. marneffei* in eryngial (0 μg/ml) after 48 hr.

Fig. 1B. Inhibitory effect of eryngial (39 μg/ml, MIC) on *P. marneffei* after 48 hr.

Fig. 1C. Growth of *C. neoformans* in eryngial (0 μg/ml) after 48 hr.

Fig. 1D. Inhibitory effect of eryngial (78 μg/ml, MIC) on *C. neoformans* after 48 hr.

Fig. 1E. Growth of *C. albicans* in eryngial (0 μg/ml) after 48 hr.

Fig. 1F. Inhibitory effect of eryngial (391 μg/ml, MIC) on *C. albicans* after 48 hr.

METHODS OF TREATING INFECTIOUS DISEASES

CROSS REFERENCE TO RELATED APPLICATIONS

This patent application is a divisional application of, and claims priority to, U.S. patent application Ser. No. 13/028,279 filed on Feb. 16, 2011, entitled "METHODS OF TREATING INFECTIOUS DISEASES, which is a divisional application of, and claims priority to, U.S. Pat. No. 7,910,114, filed on Aug. 15, 2007, entitled "METHODS OF TREATING INFECTIOUS DISEASES".

BACKGROUND OF THE INVENTION

Field of the Invention

The present invention relates to the treatment of infectious diseases and, more particularly, to methods for treating infectious diseases in humans and other mammals caused by parasitic trypanosomes, bacteria, fungi and parasitic nematodes.

Description of the Prior Art

Infectious diseases caused by protozoa, parasitic nematodes, bacteria and fungi, are a major health issue worldwide in spite of decades of development and use of antimicrobial agents to control and treat such diseases.

Antibacterial agents have been in use since the 1940's with great success, but development of drug resistance by pathogenic bacteria has gone hand in hand with that use. Currently, multidrug resistant strains of many bacteria present a serious problem for treating infectious diseases. Thus, the need for new antibacterial drugs is great. (Payne, D. et al., *Curr. Opinion. Micro.*, 7:435-8, 2004) In particular, gram positive bacteria such as *Staphylococcus aureus*, *Enterococcus faecalis*, and *Streptococcus pyogenes* are widespread and cause a great diversity of infections and diseases in humans and animals. The diseases range from minor skin infections to life-threatening pneumonias and wound infections. (Tortora, G. J. et al., 2007. Microbiology: An Introduction, 9th ed., Pearson Benjamin Cummings, San Francisco Calif.). Drug resistant strains of *S. aureus*, including methicillin resistant *S. aureus* (MRSA) and, more recently, vancomycin resistant *S. aureus* (VRSA), are a major health threat. Vancomycin resistant *Enterococcus* (VRE) is another serious problem in human health. We are reaching a stage where there are no drugs available to treat some of these serious and life-threatening infections. (Moellering, R. C., Jr., et al., *Amer. J. Medicine*, 120(7):S4-S25, 2007.)

Fungal infections are perhaps even more of an issue because the number of effective antifungal drugs is limited to start with, and development of drug resistance is also an issue for these microbes. Treatment of systemic or disseminated fungal infections has a high failure rate, creating a large burden of morbidity and mortality for these infections, especially among immunocompromised individuals. Additionally, antifungal agents frequently have serious side effects that limit their usefulness and make treating of fungal infections even more challenging.

Current drug development tends to concentrate on investigating existing categories of antibacterial or antifungal agents rather than identifying novel or new types of drugs. Additionally, many pharmaceutical companies have reduced their efforts in drug development for antimicrobial agents so that there are few new drugs in the pipeline for development. (Walsh, C., *Nature Reviews Microbiology* 1:65-70, 2003) Natural products have traditionally been a source of new types of drugs, although that approach has lessened in recent years as the number of new drugs found from natural sources has been limited. Most antimicrobial agents derived from natural sources come from other microorganisms, although a few have been developed from nonmicrobial sources.

For hundreds and even thousands of years, medicinal plants having antimicrobial activity have been used in folklore medicine across the world, a practice generally referred to as "folk medicine" or "traditional medicine" for treating a myriad of ailments including parasitic nematode infections (Dagar, H. S. et al., *Economic Botany*, 45:114-119, 1991). Scientific investigations have led to the discovery of many plant-based drugs, such as quinine and artemisinin, which are well-known antimalarial derivatives from the Cinchona bark and *Artemisia annua*, respectively (Curtis, C. F. et al., Natural and synthetic repellants. In: Curtis C. F. (Ed.) *Appropriate technology in vector control*. CRC Press, 76-92, 1990; Bodeker, G. et al., *Health in the Commonwealth*, 9:287-289, 1998). Other plant-, D. I., *Transactions of the Royal Society of Tropical Medicine and Hygiene*, Supplement, 88: 17-19, 1994; Gruber, J. W. et al., *Laboratory Medicine*, based drugs include vinblastine, camptothecin, pancrastistatin, canasol, morphine from the opium poppy and reserpine, a hypotensive alkaloid from Indian snakeroot (Phillipson 27(2): 100-108, 1996). Drug development, however, has not kept pace with the evolution of some microorganisms and there still are no effective drugs for some types of infectious diseases.

For example, parasitic nematodes have long presented significant public health problems. There are approximately 15,000 nematodes of worldwide distribution, which parasitize both plants and animals (Croll, N. A. et al., 1977, *Biology of nematodes*, Blackie and Son, Glasgow). Many of these parasites are problematic because of their pathological effects on their hosts. For example, the hookworms, such as *Ancylostoma duodenale* and *Ancylostoma caninum*, are important gastrointestinal nematode parasites of humans and of both food and companion animals. These hematophagous organisms are the causative agents of severe anemia in humans, with accompanying impairment of physical growth and cognitive development (Granzer, M. et al., *International Journal of Parasitology*, 21(4), 429-440, 1991).

*Strongyloides stercoralis*, a gastrointestinal parasitic nematode of dogs, humans and other primates, was first described by Nolmand in 1876 and afflicts 30 to 300 million people in 70 countries. *S. stercoralis* infections can be exceedingly chronic and can persist in humans for thirty years or more (Grove, D. I., Strongyloidiasis, In: Warren. K. S. and Mahmoud. A. A. (Eds.), *Tropical and Geographic Medicine*, New York: McGraw Hill, 393-399, 1990). Although chronic infections are asymptomatic in healthy individuals, poor nutrition, ill health and/or immunosuppressive therapy can exacerbate infections, giving rise to disseminated strongyloidiasis, which can be fatal (Mansfield, L. S. et al., (1992), *American Journal of Tropical Medicine and Hygiene*, 47(6):830-836, 1992).

*Haemonchus contortus* is a highly pathogenic, economically important, gastric parasitic nematode of ruminants, including goats, sheep and cattle. This passively ingested parasite poses a worldwide threat to the goat industry, particularly in sub-temperate and temperate regions like the Southeastern United States, where infections are more prevalent. Infected goats commonly present with anemia, diarrhea, dehydration, and peripheral and internal fluid accumulation. They also have lower growth rates, markedly reduced reproductive performance and have higher rates of illness and death. Other parasitic nematodes, such as *Paras-*

*trongyloides trichosuri*, are considered important because they could be sources of biological control agents. *P. trichosuri* is a parasite-specific nematode of marsupial brushtail possums, which are a major environmental and agricultural pest in New Zealand. *P. trichosuri* is being evaluated as a potential self-disseminating delivery system for engineered fertility control vaccines in possums (Cowan, P. E. et al., *New Zealand Journal of Zoology*, 32:9-16, 2005). The pathological effects of infections by parasitic nematodes, however, far outweigh any associated potential benefits.

A variety of commercial anthelmintics has been developed to control and prevent parasitic nematode infections in humans and animals. Among these are tetramisole, levamisole, praziquantel, doramectin, the benzimidazoles, which include thiabendazole and albendazole, and ivermectin. Some of these drugs are known for their effective treatment of helminth infections. For example, ivermectin, a broad-spectrum drug, is highly effective against many parasitic nematodes including *Onchocerca volvulus, H. contortus*, hookworms and *S. stercoralis* infections in humans and animals. It also has activity against insects and acarines. Albendazole is effective against *A. caninum* and, along with tetramisole, has demonstrated 100% efficacy rates against *H. contortus* infections. Doramectin was shown to reduce *P. trichosuri* infections in possums by 99%.

However, while some anthelmintics are remarkable in their treatment, others have demonstrated poor efficacy. For example, thiabendazole has been the drug of choice for treating strongyloidiasis, but its relative high cost, poor efficacy and associated unpleasant side effects have militated against its use, particularly in third world countries of the tropics where infections are most prevalent. Along with the rise of drug resistance by parasitic nematodes, the search for alternative sources of treatment is an urgent on-going process. For example, high-level anthelmintic resistance has been demonstrated by *A. caninum* against pyrantel (Kopp, S. R. et al., *Veterinary Parasitology*, 143(3-4): 299-304, 2007), and *H. contortus* has exhibited resistance against the benzimidazoles (Tiwari, J. et al., *Veterinary Parasitology*, 138 (3-4): 301-307, 2006) and ivermectin (Gill, J. H. et al., *International Journal of Parasitology*, 21(7), 771-776, 1991; Vickers, M. et al., *New Zealand Veterinary Journal*, 49(3): 101-105(5), 2001).

In Jamaican Letters Patent 3325, entitled "Medicaments for the treatment of *Strongyloides stercoralis* infections [anthelmintic activity of E-2-dodecenal, derived from *Eryngium foetidum (Ammiaceae)*, against *Strongyloides stercoralis (Nematoda)*]," issued Sep. 23, 2002, there is disclosed anthelmintic activity of trans-2-dodecenal derived from *Eryngium foetidum* against the parasitic nematode *Strongyloides stercoralis*. This patent discloses an in vitro study of trans-2-dodecenal (eryngial) taken for various durations of time, but does not disclose dose-response parameters for eryngial against *S. stercoralis*.

Another example of a class of parasitic microorganisms is parasitic trypanosomes. Currently, there are very few active agents to treat diseases caused by these microorganisms. The drugs that are available are expensive and often have associated side effects that militate against their use by infected individuals. More worrisome is the increase in the number of drug-resistant trypanosomes (Kaminsky, R. et al., *Acta Tropica*, 54:279-289, 1993.).

In the past, plant compounds have been shown to be somewhat successful in displaying anti-trypanosomal properties. For example, muzigadial, derived from a Ugandan medicinal plant (*Warburgia ugandensis*), has shown trypanocidal characteristics similar to diminazene aceturate and geneticin. Both are popular anti-trypanosomal agents (Olila, D. et al., *African Journal of Biotechnology*, 4: 134-137, 2005).

It is difficult, however, to find compounds that are effective against trypanosomes because they have a variant-specific glycoprotein (VSG) coat. Effective treatment further is complicated by the trypanosome's ability to switch from one VSG to another (Rifkin, M. R., *National Academy of Sciences*, 87:801-805, 1990).

Trypanosomes are flagellated protozoa of the genus *Trypanosoma*. Various species of *Trypanosoma* cause numerous diseases in humans and other mammals. For example, *Trypanosoma brucei gambiense* and *Trypanosoma brucie rhodesiense* cause trypanosomiasis, also referred to as African sleeping sickness, transmitted by tsetse flies of the genus *Glossina*.

In South America, a different trypanosome, *Trypanosoma cruzi*, causes Chagas disease, which affects the nervous system and heart. This parasite is not transmitted by tsetse flies but by a different type of blood-sucking arthropod, *Triatoma infestans*, also referred to as the triatomine kissing bug. (Schmidt, G. D. and Roberts, L. S., 1989, *Foundations of Parasitology*, $4^{th}$ ed. St. Louis: Times Mirror/Mosby, p. 55-79). Other species, restricted in distribution to Africa and Asia, cause diseases of horses and cattle. Control measures include elimination or reduction of the insect carrier populations and measures to reduce the likelihood of bites.

Trypanosomes have a complex life cycle. They use invertebrate hosts, such as insects and leeches, which then transmit the parasite to vertebrate animals. Domesticated animals, such as dogs, cats and cattle, can serve as reservoir hosts for these parasites before they are passed to humans (Abenda, J. N., *African J. Biotechnology*, 4: 134-137, 2005). For example, *T. cruzi* exists as a long, slender trypomastigote form that circulates in a vertebrate animal's blood. Trypomastigotes are ingested by an insect vector (triatomine bugs) during a blood meal. The parasites migrate to the insect's midgut where they change to an epimastigote form, which subsequently multiplies to become metacyclic trypanosomes. These form s are short and stumpy and are passed via feces from the insect vector and deposited on the skin of an unsuspecting vertebrate. They enter the vertebrate through mucus membranes or scratched skin and travel in the blood to muscle tissue. In the muscle tissue, they lose their flagella, change to an amastigote form, reproduce and then change to a trypomastigote form. These then enter and circulate in the vertebrate's blood stream where they can be ingested by an insect during a blood meal. (Schmidt, G. D. and Roberts, L. S., 1989, *Foundations of Parasitology*, $4^{th}$ ed., St. Louis: Times Mirror/Mosby, p. 55-79).

There is a need, therefore, for new types of antimicrobial drugs to treat infections caused by parasitic protozoa, bacteria, fungi and nematodes.

SUMMARY OF THE INVENTION

The present invention meets this need by providing a method of treating a human or other mammal for a parasitic microorganism by administering an effective amount of a $C_8$-$C_{16}$-alpha, beta-unsaturated aliphatic aldehyde, preferably a $C_{10}$-$C_{14}$-alpha, beta-unsaturated aliphatic aldehyde, and most preferably trans-2-dodecenal (also referred to as "eryngial") to the human or other mammal. The method includes treating a human or other mammal which is infected or is believed to be infected with the parasite. The method further includes administering the therapeutically effective amount of eryngial in unit dosage form.

The trans-2-dodecenal compound can be isolated from plant sources such as *Eryngium foetidum* and *Coriandrum sativum*.

In an aspect of the present invention, there is provided a method of treating a mammal for a parasite of the genus *Trypanosoma*, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

The genus *Trypanosoma* includes *Trypanosoma rangeli, Trypanosoma mega, Trypanosoma avium, Trypanosoma conorhini, Trypanosoma brucei gambiense, Trypanosoma brucei rhodesiense* and *Trypanosoma cruzi*.

In another aspect of the present invention, there is provided a method of treating a mammal for *Enterococcus faecalis* or *Streptococcus pyogenes* bacteria, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

In another aspect of the present invention, there is provided a method of treating a mammal for a fungus selected from *Cryptococcus neoformans, Microsporum gypseum* or *Penicillium marneffei*, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

In another aspect of the present invention, there is provided a method of treating a mammal for a parasitic nematode selected from the group consisting of *Parastrongyloides trichosuri, Haemonchus contortus* and *Ancylostoma caninum*, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

The above methods include treating a human or other mammal which is infected with or is believed to be infected with the parasite. The above methods further include administering the therapeutically effective amount of eryngial in unit dosage form.

"Mammal" as used herein is meant to include humans.

When treating *Parastrongyloides trichosuri* in vitro, the therapeutically effective amount of the $C_8$-$C_{16}$-alpha, beta-unsaturated aliphatic aldehyde ranges from between about 0.005 and about 0.8 mg/ml, preferably from between about 0.007 and about 0.7 mg/ml, and more preferably from between about 0.22 and about 0.52 mg/ml.

When treating *Haemonchus contortus* in vitro, the therapeutically effective amount of the $C_8$-$C_{16}$-alpha, beta-unsaturated aliphatic aldehyde ranges from between about 0.07 and about 8.0 mg/ml, preferably from between about 1.0 and about 7.0 mg/ml, and more preferably from between about 2.0 and about 6.0 mg/ml.

When treating *Ancylostoma caninum* in vitro, the therapeutically effective amount of the $C_8$-$C_{16}$-alpha, beta-unsaturated aliphatic aldehyde ranges from between about 0.4 and about 4.0 mg/ml, preferably from between about 0.6 and about 3.0 mg/ml, and more preferably from between about 0.9 and about 2.0 mg/ml.

Accordingly, it is an object of the present invention to provide a safe and effective treatment for a human or other mammal infected with or believed to be infected with a parasitic microorganism.

It is another object of the present invention to provide a method of treating a human or other mammal infected with or believed to be infected with the parasitic protozoa *Trypanosoma rangeli, Trypanosoma mega, Trypanosoma avium, Trypanosoma conorhini, Trypanosoma brucei gambiense, Trypanosoma brucei rhodesiense* and *Trypanosoma cruzi*.

It is another object of the present invention to provide a method of treating a human or other mammal infected with or believed to be infected with larvae of parasitic nematodes such as *Strongyloides stercoralis; Ancylostoma caninum; Parastrongyloides trichosuri*; or *Haemonchus contortus*.

It is another object of the present invention to provide a method of treating a human or other mammal infected with or believed to be infected with the bacteria *Enterococcus faecalis* or *Streptococcus pyogenes*.

It is another object of the present invention to provide a method of treating a human or other mammal infected with or believed to be infected with the fungi *Cryptococcus neoformans, Microsporum gypseum* or *Penicillium marneffei*.

BRIEF DESCRIPTION OF THE DRAWINGS

A full understanding of the invention can be gained from the following description of the preferred embodiments when read in conjunction with the accompanying drawings in which:

FIG. 1 shows photomicrographs of the inhibitory effect of eryngial on three different fungi species.

DESCRIPTION OF THE PREFERRED EMBODIMENTS

The present invention provides a method of treating a human or other mammal for a parasitic microorganism by administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and most preferably trans-2-dodecenal compound to the human or other mammal. The method includes treating a human or other mammal which is infected with or is believed to be infected with the parasite. The method further includes administering the therapeutically effective amount in unit dosage form.

As used herein, the term "trans-2-dodecenal" (also referred to as E-2-dodecenal) is interchangeable with the term "eryngial."

As used herein, "mammals" include humans.

As used herein, the term "therapeutically effective amount" refers to that amount of eryngial required to bring about a desired effect in a human or other mammal. In all instances, at its most basic level, the desired effect is the permanent immobilization and/or killing of the particular parasitic microorganism that has infected or is believed to have infected a human or other mammal after the human or other mammal has been exposed to the particular parasitic microorganism.

The trans-2-dodecenal compound can be isolated from plant sources such as *Eryngium foetidum* and *Coriandrum sativum*.

In an embodiment of the present invention, there is provided a method of treating a mammal for a parasite of the genus *Trypanosoma*, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

The genus *Trypanosoma* includes *Trypanosoma rangeli*, *Trypanosoma mega*, *Trypanosoma avium*, *Trypanosoma conorhini*, *Trypanosoma brucei gambiense*, *Trypanosoma brucei rhodesiense* and *Trypanosoma cruzi*.

In another embodiment of the present invention, there is provided a method of treating a mammal for *Enterococcus faecalis* or *Streptococcus pyogenes* bacterium, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

In a further embodiment of the present invention, there is provided a method of treating a mammal for a fungus selected from *Cryptococcus neoformans*, *Microsporum gypseum* or *Penicillium marneffei*, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

In still a further embodiment of the present invention, there is provided a method of treating a mammal for a parasitic nematode selected from the group consisting of *Parastrongyloides trichosuri*, *Haemonchus contortus* and *Ancylostoma caninum*, comprising administering a therapeutically effective amount of a $C_8$-$C_{16}$-alpha, beta-unsaturated aliphatic aldehyde, preferably a $C_{10}$-$C_{14}$-alpha, beta-unsaturated aliphatic aldehyde, and more preferably trans-2-dodecenal, to the mammal.

When treating *Parastrongyloides trichosuri* in vitro, the therapeutically effective amount of the $C_8$-$C_{16}$-alpha, beta-unsaturated aliphatic aldehyde ranges from between about 0.005 and about 0.8 mg/ml, preferably from between about 0.007 and about 0.7 mg/ml, and more preferably from between about 0.22 and about 0.52 mg/ml.

When treating *Haemonchus contortus* in vitro, the therapeutically effective amount of the $C_8$-$C_{16}$-alpha, beta-unsaturated aliphatic aldehyde ranges from between about 0.07 and about 8.0 mg/ml, preferably from between about 1.0 and about 7.0 mg/ml, and more preferably from between about 2.0 and about 6.0 mg/ml.

When treating *Ancylostoma caninum* in vitro, the therapeutically effective amount of the $C_8$-$C_{16}$-alpha, beta-unsaturated aliphatic aldehyde ranges from between about 0.4 and about 4.0 mg/ml, preferably from between about 0.6 and about 3.0 mg/ml, and more preferably from between about 0.9 and about 2.0 mg/ml.

The parasitic nematode may further include *Strongyloides stercoralis*, wherein the therapeutically effective amount of the $C_8$-$C_{16}$-alpha, beta-unsaturated aliphatic aldehyde that is administered in vitro to treat *Strongyloides stercoralis* ranges from between about 0.05 and about 0.4 mg/ml, preferably from between about 0.07 and about 0.3 mg/ml, and more preferably from between about 0.12 and about 0.25 mg/ml.

The route of administration of the $C_8$-$C_{16}$-alpha, beta-unsaturated aliphatic aldehyde compound can be oral; parenteral, such as intravenous, intramuscular or subcutaneous; or topical.

When the route of administration is oral, it can be administered in the form of hard or soft shell gelatin capsules, tablets or lozenges.

EXAMPLES

The present invention is more particularly described in the following non-limiting examples, which are intended to be illustrative only, as numerous modifications and variations therein will be apparent to those skilled in the art.

Example 1

Anthelmintic Activity and Extraction of Eryngial from *Eryngium Foetidum*

1. Anthelmintic Activity of Eryngial

The anthelmintic activity of eryngial was discovered as follows. The crude extracts from a total of twenty-five different medicinal plants in Jamaica were screened for antiworm activity. The crude extract of eryngial was observed to be the most effective. The crude extract of eryngial was scrutinized further to identify the source of activity. This was preformed first by separating the crude extract into consecutive non-polar, medium polar and polar crude extracts. Each extract was bioassayed in vitro. The non-polar fraction was identified as the most active of the three crude extracts from *E. foetidum*. The non-polar crude extract was further investigated and was identified as being the source of eryngial.

2. Extraction of Eryngial from *Eryngium Foetidum*

Identification, isolation and partial chemical characterization of eryngial was accomplished as follows. The non-polar crude extract was removed from fresh whole plants using petroleum ether (PE) as the extraction solvent. To extract the non-polar crude extract, the following steps were performed:
1. Fresh plant material was collected and washed to remove debris.
2. The plant material was dried briefly to remove excess water.
3. The plant material then was chopped into small pieces and its mass (g) was determined.
4. A known volume of PE was added and then stored for 12 hr in a light free container.
5. The plant material then was blended and placed again in a light free container.
6. The plant material underwent extraction for 24 hr.
7. The PE extract was collected and any water present was removed using a separatory funnel.
8. The PE extract was stored in a light free container and refrigerated.
9. A known volume of PE again was added and steps (6) and (7) were repeated.
10. The PE crude extracts were pooled and concentrated by rotary evaporation to remove the solvent.
11. Yield of the PE crude extract was determined Compounds in the non-polar extract were separated using thin layer chromatography (TLC) and column chromatography (CC) techniques. The compounds were bioassayed and the most potent compound was identified. This compound was partially chemically characterized by nuclear magnetic resonance (NMR) and mass spectral analysis. Its chemical structure was determined to be trans-2-dodecenal and it was given the name eryngial because it was an aldehyde and its source was *E. foetidum*.

Example 2

Antitrypanosomal Potential of Eryngial using *Trypanosoma Mega*, *Trypanosoma Rangeli*, *Trypanosoma Conorhini* and *Trypanosoma Avium* In Vitro The antitrypanosomal potential of ernygial was investigated in vitro using the trypomastigote form of the following Trypanosome species: *Trypanosoma mega*, *Trypanosoma rangeli*, *Trypanosoma conorhini* and *Trypanosoma avium*.

1. Materials and Methods

In this study, 75 µl of Locke's nematode saline (L.N.S.) solution with approximately $1.0 \times 10^5$ trypomastigotes/ml of each organism were placed in 15 wells of a cell culture plate. For *T. mega*, *T. conorhini* and *T. avium*, stock concentrations of eryngial (1, 2, 3 and 4 mg/ml) with 0.04% (w/v) Triton X-100 were prepared in L.N.S. Triton X-100 acted as an emulsifier for eryngial. Triplicate samples of each eryngial concentration were prepared by adding 75 µl of the stock to the wells with trypomastigotes of each species. The number of trypanosomes in each well therefore approximated $5 \times 10^4$/ml, while final concentrations of eryngial in the wells were 0.5, 1.0, 1.5, and 2.0 mg/ml, respectively. Each sample also had 0.02% Trition X-100. The control samples had no eryngial. The number of trypomastigotes that were present in 20 µl sub-samples of each well was determined using a hemacytometer at 0, 24 and 48 hr. A count of the trypanosomes in each grid was recorded and the average number of organisms per milliliter was determined. The above procedure was repeated to determine the effect of eryngial on *T. rangeli*. However, the final concentration of eryngial, the test compound, ranged from 0.15 to 0.9 mg/ml.

A short-term behavioral study also was conducted by adding 75 µl of eryngial (1%) and Triton X-100 (0.04%) to 75 µl of L.N.S. with *T. avium* ($1.0 \times 10^5$ trypomastigotes/ml). The swimming behavior and maneuverability of the organisms were observed microscopically in triplicate samples at 15-minute intervals for 1 hr. This was recorded with a digital video camera.

The data obtained from the 24 hr interval bioassay studies were subjected to Probit Analysis to determine the concentration of eryngial that killed 50% ($LC_{50}$) and 95% ($LC_{95}$) of each trypanosome species.

2. Results

The $LC_{50}$ and $LC_{95}$ values of eryngial against the trypanosomes after 24 hr are shown in Table 1. For *T. rangeli* trypomastigotes, the $LC_{50}$ of eryngial (0.17 mg/ml) was significantly different (p, 0.05) from the $LC_{95}$ (0.45 mg/ml) value. This also was true for the other trypanosome species *T. mega*, *T. conorhini* and *T. avium*. The $LC_{50}$ of *T. rangeli* (0.17 mg/ml) was significantly different from the $LC_{50}$ of *T. mega* (0.81 mg/ml), *T. conorhini* (0.85 mg/ml) and *T. avium* (1.91 mg/ml). The latter three species, however, were not significantly different from each other. The $LC_{95}$ of *T. rangeli* (0.45 mg/ml) also was significantly different from the $LC_{95}$ of *T. mega* (2.85 mg/ml), *T. conorhini* (2.91 mg/ml) and *T. avium* (3.12 mg/ml). The 24 hr $LC_{95}$ of *T. mega*, *T. conorhini* and *T. avium* were not significantly different from each other.

TABLE 1

Concentrations (mg/ml) of eryngial that killed 50% ($LC_{50}$) and 95% ($LC_{95}$) of *Trypanosoma rangeli*, *Trypanosoma mega*, *Trypanosoma conorhini* and *Trypanosoma avium*, respectively, after 24 hr in vitro

| | Eryngial | |
|---|---|---|
| Organism | 24 hr $LC_{50}$ (mg/ml) ± 95% confidence intervals | 24 hr $LC_{95}$ (mg/ml) ± 95% confidence intervals |
| *T. rangeli* | 0.17 (0.14-0.19) | 0.45 (0.38-0.55) |
| *T. mega* | 0.81 (0.66-0.93) | 2.85 (2.20-4.40) |
| *T. conorhini* | 0.85 (0.70-0.99) | 2.91 (2.22-4.69) |
| *T. avium* | 1.19 (0.96-1.40) | 3.12 (2.57-4.16) |

The 48 hr $LC_{50}$ and $LC_{95}$ values of eryngial against the trypanosomes are shown in Table 2. The $LC_{50}$ of eryngial (0.09 mg/ml) against *T. rangeli* trypomastigotes was significantly different from the corresponding $LC_{95}$ (0.31 mg/ml) value. The $LC_{50}$ of *T. rangeli* also was significantly lower than the $LC_{50}$ of *T. conorhini* (0.50 mg/ml), *T. avium* (0.68 mg/ml) and *T. mega* (0.76 mg/ml). The $LC_{50}$ of *T. conorhini* was significantly different from the $LC_{50}$ of *T. avium* and *T. mega*, which were not significantly different from each other. The 48 hr $LC_{95}$ of *T. rangeli* (0.31 mg/ml) also was significantly different from the $LC_{95}$ of *T. conorhini* (1.14 mg/ml), *T. avium* (1.02 mg/ml) and *T. mega* (2.31 mg/ml). Whereas the $LC_{95}$ of *T. conorhini* and *T. avium* were not significantly different from each other, both values differed significantly from that of *T. mega*.

TABLE 2

Concentrations (mg/ml) of eryngial that killed 50% ($LC_{50}$) and 95% ($LC_{95}$) of *Trypanosoma rangeli*, *Trypanosoma mega*, *Trypanosoma conorhini* and *Trypanosoma avium*, respectively, after 48 hr in vitro

| | Eryngial | |
|---|---|---|
| Organism | 48 hr $LC_{50}$ (mg/ml) ± 95% confidence intervals | 48 hr $LC_{95}$ (mg/ml) ± 95% confidence intervals |
| *T. rangeli* | 0.09 (0.05-0.12) | 0.31 (0.26-0.43) |
| *T. mega* | 0.50 (0.39-0.58) | 1.14 (0.95-1.56) |
| *T. conorhini* | 0.68 (0.62-0.75) | 1.02 (0.91-1.20) |
| *T. avium* | 0.76 (0.63-0.87) | 2.31 (1.87-3.26) |

In the short-term behavioral study, it was noted that the *T. avium* trypomastigotes swam vigorously with rapid, whip-like undulations of each organism's flagellum at the beginning of the bioassay. They typically darted from one point to another across the field of view. However, with time, the rate of movement of the flagellum slowed and maneuverability of the trypanosomes became reduced until movement was completely stopped.

Example 3

An In Vitro Antibacterial and Antifungal Study Using Eryngial

This investigation was undertaken to examine the antifungal and antibacterial properties of eryngial when tested against a variety of medically important bacteria and fungi.

1. Materials and Methods a. Cell Cultures

Bacterial cultures were obtained from the American Type Culture Collection (ATCC), except for *Streptococcus pyogenes*, which was started from a Difco Bactrol disc. The other organisms were *Enterococcus faecalis, Staphylococcus aureus, Escherichia coli, Salmonella typhimurium* and *Pseudomonas aeruginosa*. Cultures were grown in Luria-Bertani (LB) broth. Fungi were obtained from Carolina Biological Supply Company (*Aspergillus niger, Candida albicans* and *Cryptococcus neoformans*); Presque Isle Cultures, Erie Pa. (*Microsporum gypseum*); or from ATCC (*Penicillium marneffei*). Fungal cultures were maintained in Sabouraud dextrose broth (SDB) or agar (SDA). All media components came from Difco.

Eryngial (trans-2-dodecenal), originally isolated from *Eryngium foetidum*, was supplied by the Organic Laboratory, Dept. of Chemistry, University of the West Indies (Mona Campus), Jamaica.

b. Determining Minimum Inhibitory Concentration (MIC)

Tests were done in flat-bottomed 96 well cell culture plates (Costar). All samples were done in duplicate. Eryngial was suspended in culture medium plus 0.04% Triton-X to make a 2% (20 mg/ml) suspension, which was passed through a 0.22 μm filter to make a uniform emulsion. Serial doubling dilutions of eryngial in culture medium plus 0.04% Triton-X were prepared, and 75 μl was added to each well. 75 μl of cell or spore suspensions in culture medium also were added to each well. The final concentration of Triton-X was 0.02%, and the final concentration of eryngial was 1% (10 mg/ml) at the highest concentration tested.

Dimethyl sulfoxide (DMSO) also was used as a solvent for eryngial. A solution of 12.5% eryngial in DMSO was the initial solution. Doubling dilutions were carried out in DMSO. The DMSO-eryngial solutions were diluted 100-fold into growth medium, resulting in a final concentration of 1% DMSO, and 0.125% (1,250 μg/ml) eryngial as the highest concentration tested.

Overnight bacterial cultures in LB medium were diluted into fresh LB to an $OD_{600}$ of 0.02 to 0.03, and then diluted 1000-fold again in LB. This resulted in several thousand cells per 75 μl added to each well. Blank wells for each concentration of eryngial were prepared with plain culture medium added.

The 96 well plates were incubated at 37° for 24 hr (in a candle jar for *S. pyogenes*), and the $OD_{630}$ was read on an EL800 universal microplate reader (Bio-Tek Instruments). Readings from duplicate wells were averaged, and readings from duplicate blank wells for each concentration of eryngial were subtracted to generate the final values. The minimum inhibitory concentration (MIC, μg/ml) was defined as the well with the highest dilution of eryngial in which no growth was observed.

The yeast form fungi, *Candida albicans* and *Cryptococcus neoformans*, were grown overnight in SDB. Cell density was determined by counting in a hemacytometer. Cells were diluted in fresh SDB to a density of $10^4$/ml, and 75 μl, or $7.5 \times 10^2$ cells, was added to each well. The filamentous form fungi, *Aspergillus niger, Microsporum gypseum* and *Penicillium marneffei*, were grown on SDA until spores formed. The surface of the culture was rinsed vigorously with sterile distilled water to make a spore suspension, which was counted with a hemacytometer. The spores were diluted into SDB at $10^4$/ml, and 75 μl, or $7.5 \times 10^2$ spores, were added to each well. The 96 well plates were incubated at room temperature in a humidified chamber for up to 96 hr, and culture growth was monitored microscopically. Growth was documented by photomicrographs at 24 hr intervals, and by determining $OD_{630}$ in the microplate reader as for the bacterial cultures.

c. Determining Minimum Bactericidal or Fungicidal Concentration

To determine whether eryngial was merely inhibiting growth of the bacteria and fungi, or whether it also was having a killing effect, the minimum bactericidal concentrations (MBC, μg/ml) or minimum fungicidal concentrations (MFC, μg/ml) were determined. This was done by removing a 50 μl sample from a well after 24 hr (bacteria) or 96 hr (fungi) and diluting the samples in 5 ml of fresh culture medium. These tubes then were incubated at the appropriate temperature for 24-96 hr and observed for any signs of growth.

2. Results

The MICs and MBCs of eryngial against the bacterial cultures after 24 hr of exposure are shown in Table 3. All the gram-positive bacteria (*S. aureus, S. pyogenes* and *E. faecalis*) but none of the gram-negative bacteria (*E. coli, S. typhimurium* and *P. aeruginosa*) were inhibited by eryngial. The MICs also were the MBCs for the respective organisms. All the tests were done using 0.02% Triton X-100. DMSO was used as the solvent for tests with *S. pyogenes*. The MICs and MBCs of eryngial in DMSO for *S. aureus* and *E. faecalis* were similar to the respective values that are shown in Table 3.

TABLE 3

MICs and MBCs of eryngial against *S. aureus, S. pyogenes*, and *E. faecalis* after 24 hr in vitro

| Bacterial Organisms | Eryngial MIC (μg/ml) | Eryngial MBC (μg/ml) |
|---|---|---|
| *S. aureus* | 78 | 78 |
| *S. pyogenes* | 156 | 156 |
| *E. faecalis* | 313 | 313 |

The MICs and MFCs of eryngial against the fungi *A. niger, C. albicans, C. neoformans, M. gypseum* and *P. marneffei* are shown in Table 4.

TABLE 4

MICs and MFCs of eryngial against *M. gypseum, P. marneffei, C. neoformans* and *C. albicans* after 48-96 hr in vitro

| Fungi | Eryngial MIC (μg/ml) | Eryngial MBC (μg/ml) |
|---|---|---|
| *M. gypseum* | 39 | 39 |
| *P. marneffei* | 39 | 39 |
| *C. neoformans* | 78 | 78 |
| *C. albicans* | 391 | 391 |

Figure 1A:
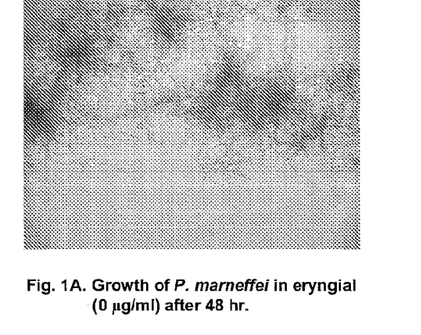
FIG. 1A shows the growth of *P. marneffei* in 0 µg/ml eryngial after 48 hr.
Figure 1B:
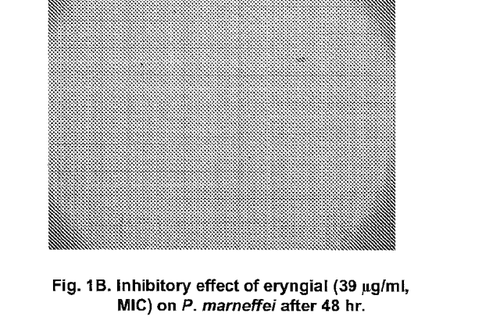
FIG. 1B shows the inhibitory effect of eryngial (39 µg/ml, MIC) on *P. marneffei* after 48 hr.
Figure 1C:
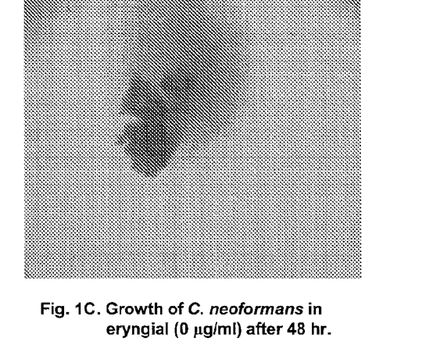
FIG. 1C shows the growth of *C. neoformans* in 0 µg/ml eryngial after 48 hr.
Figure 1D:
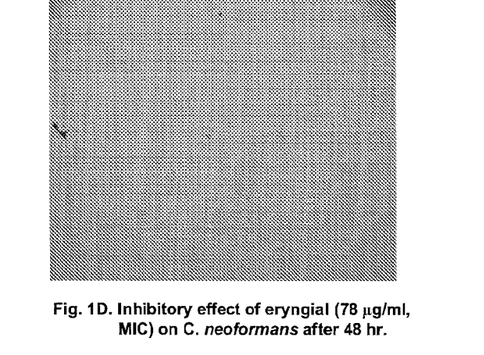
FIG. 1D shows the inhibitory effect of eryngial (78 µg/ml, MIC) on *C. neoformans* after 48 hr.
Figure 1E:
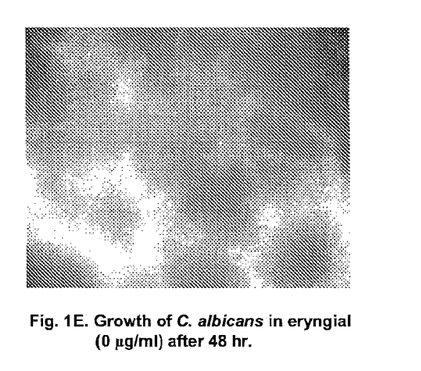
FIG. 1E shows the growth of *C. albicans* in 0 µg/ml eryngial after 48 hr.
Figure 1F:
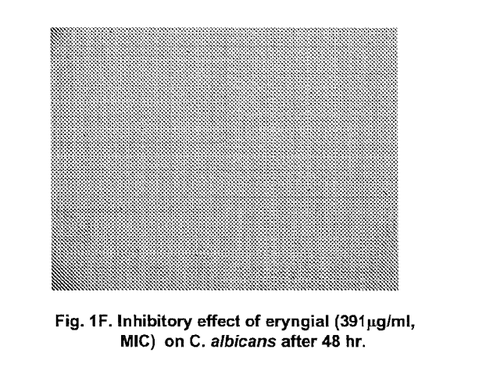
FIG. 1F shows the inhibitory effect of eryngial (391 µg/ml, MIC) on *C. albicans* after 48 hr.

Minimum inhibitory and minimum fungicidal concentrations of eryngial for *A. niger* were not determined as growth, albeit reduced, occurred in all dilutions of the test compound. FIG. 1 provides pictures of the inhibitory effect of eryngial on *P. marneffei* (FIGS. 1A, B), *C. neoformans* (FIGS. 1C, D) and *C. albicans* (FIGS. 1E, F) after 48 hr inoculation.

Example 4

Determination of Immobilization and Lethal Doses of Four Infective Parasitic Nematode Larvae 1. Introduction Scientists have long investigated plants as potential sources of drugs. In particular, a variety of plants has been shown to possess anthelmintic activity. For example, extracts from the plant *Khaya senegalensis* have been shown to cause a decrease in larval viability of ovine gastrointestinal nematodes (Ademola, I. et al., Veterinary Parasitology, 122(2):154-164, 2004). Evaluation of the anthelmintic activity of *Khaya senegalensis* extract against gastrointestinal nematodes of sheep: in vitro and in vivo studies). In a study by Robinson et al. (*West Indian Medical Journal*, 39(4), 213-217, 1990), the anthelmintic activities of six Jamaican plants were demonstrated in vitro, using *S. stercoralis* infective larvae. This finding precipitated the screening of twenty-five Jamaican medicinal plants, which led to the discovery of eryngial.

Eryngial (trans-2-dodecenal), a non-polar volatile compound of *Eryngium foetidum L. Apiaceae*, was discovered by Forbes et al. (unpublished) for its anthelmintic activity using *Strongyloides stercoralis* infective larvae. Their in vitro study demonstrated the duration or time necessary (in hours) for eryngial to inactivate the infective larvae. However, no dose-related studies have been conducted to establish eryngial as a potential broad-spectrum anthelmintic using a variety of parasitic nematodes, including *S. stercoralis*.

This investigation was undertaken to investigate eryngial as a source of an anthelmintic with broad-spectrum activity. The investigation included determining and comparing dose-related activity of eryngial with ivermectin, a broad-spectrum commercial anthelmintic.

2. Materials and Methods

Eryngial (trans-2-dodecenal) is an anthelmintic plant compound that was discovered in and chemically extracted from *Eryngium foetidum*. It was obtained from the Organic Laboratory, Department of Chemistry, The University of the West Indies (Mona), Jamaica and used for all bioassay studies.

a. Parasitic Nematodes

*Strongyloides stercoralis* infective larvae were harvested from charcoal coprocultures in nematode saline solution. The larvae were supplied by the Parasitology Laboratory, Department of Pathobiology, University of Pennsylvania. The strain of larvae was a human strain of the parasitic nematode that had been maintained for over ten years in canines by daily prednisolone treatment (2 mg/kg per os, once daily. *Parastrongyloides trichosuri* and *Ancylostoma caninum* infective larvae were also supplied by the same source as for *S. stercoralis*. *Haemonchus contortus* infective larvae were harvested from charcoal coprocultures in nematode saline solution prepared from infected sheep feces obtained from Merck Parasites Laboratory.

b. In Vitro Bioassay

The 24 hr 50% and 90% immobilization doses ($ID_{50}$ and $ID_{90}$), and 50% and 90% lethal doses ($LD_{50}$ and $LD_{90}$) of eryngial (mg/ml) were investigated in vitro using infective larvae of all four parasitic nematodes. Each species was exposed to a range of eryngial dilutions by adding known volumes of a homogeneous 'wormy' solution (infective larvae in nematode saline solution) to known volumes of an eryngial stock suspension (10 mg/ml of nematode saline solution). Each dilution, including the control (0 mg/ml eryngial), was prepared in triplicate and also contained eosin (0.01%, w/v), which was used as an indicator of mortality, and Triton X-100 (1.0%, v/v). The mechanism by which eosin indicates mortality is by absorption of the killed larvae of the eosin stain, whereas immobilized larvae do not absorb the eosin stain.

Using *S. stercoralis*, *P. trichosuri*, *H. contortus* and *A. caninum* infective larvae, eryngial dilutions, excluding the controls, ranged from 0.05 to 1.15 mg/ml; 0.01 to 1.0 mg/ml; 0.5 to 2.0 mg/ml; and 0.8 to 3.0 mg/ml, respectively. Sub-sample (10 µl) counts of larvae that were mobile, immobile but not stained and stained, were done at the start of each bioassay and at 24 hr intervals for two days. Each sub-sample contained approximately 50 infective larvae.

The 48-hr immobilization doses ($ID_{50}$ and $ID_{90}$) and lethal doses ($LD_{50}$ and $LD_{90}$) of eryngial and ivermectin also were investigated, using *S. stercoralis* and *H. contortus* infective larvae. Each bioassay was conducted as described hereinabove. Using *S. stercoralis* and *H. contortus* infective larvae, ivermectin dilutions (not including the controls) ranged from 0.03 to 0.3 mg/ml and from 0.009 to 0.1 mg/ml, respectively.

Probit analysis was used to determine 24 hr and 48 hr immobilization and lethal doses for eryngial and ivermectin, respectively.

3. Results

Table 5 shows 24 hr 50% and 90% immobilization doses (mg/ml) after 24 hr of eryngial for *P. trichosuri*, *S. stercoralis*, *H. contortus* and *A. caninum* infective larvae. The $ID_{50}$ for *P. trichosuri* (0.013), *S. stercoralis* (0.058), *H. contortus* (0.132) and *A. caninum* (0.545) were significantly different from each other. Whereas the $ID_{90}$ doses for *P. trichosuri* (0.092) and *S. stercoralis* (0.081) were not significantly different from each other, they were different from those of *H. contortus* (0.782) and *A. caninum* (0.867), which were not significantly different from each other. In all instances, the $ID_{50}$ doses were significantly lower than the corresponding $ID_{90}$ doses.

TABLE 5

Doses of eryngial required to immobilize 50% ($ID_{50}$) and 90% ($ID_{90}$) of *P. trichosuri*, *S. stercoralis*, *H. contortus* and *A. caninum* infective larvae respectively, after 24 hr in vitro

| | Eryngial | |
| --- | --- | --- |
| Parasite | 24 hr $ID_{50}$ (mg/ml) ± 95% confidence intervals | 24 hr $ID_{90}$ (mg/ml) ± 95% confidence intervals |
| *P. trichosuri* | 0.013 (0.007-0.030) | 0.092 (0.051-0.201) |
| *S. stercoralis* | 0.058 (0.054-0.061) | 0.081 (0.076-0.088) |
| *H. contortus* | 0.132 (0.078-0.186) | 0.782 (0.641-0.998) |
| *A. caninum* | 0.545 (0.440-0.641) | 0.867 (0.717-1.445) |

Table 6 shows a comparison of 50% immobilization doses (mg/ml) after 48 hr of eryngial and ivermectin using *S. stercoralis* and *H. contortus* infective larvae, respectively. Immobilization doses were not obtained for *P. trichosuri* and *A. caninum*. The $ID_{50}$ of eryngial (0.054) was significantly lower than the $ID_{50}$ of ivermectin (0.136) for *S. stercoralis* L3 larvae. However, for *H. contortus*, the converse was true, that is, the $ID_{50}$ of eryngial (0.313) was significantly higher than the $ID_{50}$ of ivermectin (0.011). Using eryngial, the 48 hr $ID_{50}$ for *S. stercoralis* (0.054) was significantly different from the 48 hr $ID_{50}$ for *H. contortus* (0.313). With ivermectin, this was also true of the 48 hr $ID_{50}$ values for *S. stercoralis* (0.136) and *H. contortus* (0.011), respectively.

TABLE 6

Doses of eryngial and ivermectin required to immobilize 50% ($ID_{50}$) of S. stercoralis and H. contortus infective larvae respectively, after 48 hr in vitro

| Parasite | Eryngial 48 hr $ID_{50}$ (mg/ml) ± 95% confidence intervals | Ivermectin 48 hr $ID_{50}$ (mg/ml) ± 95% confidence intervals |
|---|---|---|
| S. stercoralis | 0.054 (0.047-0.061) | 0.136 (0.114-0.157) |
| H. contortus | 0.313 (0.143-0.453) | 0.011 (0.001-0.022) |

Table 7 represents 90% immobilization doses (mg/ml) after 48 hr of eryngial and ivermectin for S. stercoralis and H. contortus infective larvae, respectively. Using S. stercoralis L3 larvae, the $ID_{90}$ of eryngial (0.077) was significantly lower than the $ID_{90}$ of ivermectin (0.297). Using H. contortus L3 larvae, however, the $ID_{90}$ of eryngial (0.761) was significantly higher than the $ID_{90}$ of ivermectin (0.059). The $ID_{90}$ value of eryngial (0.077) against S. stercoralis was significantly lower than its $ID_{90}$ (0.761) against H. contortus. The opposite was true for ivermectin. The $ID_{90}$ (0.297) against S. stercoralis was significantly higher than its $ID_{90}$ for H. contortus.

TABLE 7

Doses of eryngial and ivermectin required to immobilize 90% ($ID_{90}$) of S. stercoralis and H. contortus infective larvae respectively, after 48 hr in vitro

| Parasite | Eryngial 48 hr $ID_{90}$ (mg/ml) ± 95% confidence intervals | Ivermectin 48 hr $ID_{90}$ (mg/ml) ± 95% confidence intervals |
|---|---|---|
| S. stercoralis | 0.077 (0.066-0.101) | 0.297 (0.251-0.377) |
| H. contortus | 0.761 (0.530-1.488) | 0.059 (0.043-0.092) |

For both S. stercoralis and H. contortus infective larvae, the 48 hr $ID_{50}$ values of eryngial were significantly lower than its respective 48 hr $ID_{90}$ values (Tables 6 and 7). This trend was also seen for ivermectin, in which the 48 hr $ID_{50}$ values were significantly lower than the corresponding 48 hr $ID_{90}$ values (Tables 6 and 7).

Table 8 shows 50% and 90% mortality doses (mg/ml) after 24 hr of eryngial for S. stercoralis, P. trichosuri, A. caninurn and H. contortus infective larvae, respectively. Except for P. trichosuri ($ID_{50}$, 0.105), all the $LD_{50}$ values for S. stercoralis (0.085), A. caninum (0.608) and H. contortus (1.793), were significantly different from each other. The $ID_{50}$ for S. stercoralis and P. trochosuri were not significantly different from each other. The 24 hr $LD_{90}$ of eryngial for S. stercoralis (0.143) and P. trichosuri (0.297) were not significantly different from each other. They were, however, significantly different from the 24 hr $LD_{90}$ for A. caninum (1.178) and H. contortus (2.765). The $LD_{90}$ of A. caninum and H. contortus were not significantly different from each other. In all cases, except for H. contortus, for S. stercoralis, P. trichosuri and A. caninum, the respective 24 hr $LD_{50}$ values were significantly lower than the corresponding 24 hr $LD_{90}$ values.

*TABLE 8

Doses of eryngial required to kill 50% ($LD_{50}$) and 90% ($LD_{90}$) of S. stercoralis, P. trichosuri, A. caninum and H. contortus infective larvae respectively, after 24 hr in vitro

| | Eryngial | |
|---|---|---|
| Parasite | 24 hr $LD_{50}$ (mg/ml) ± 95% confidence intervals | 24 hr $LD_{90}$ (mg/ml) ± 95% confidence intervals |
| S. stercoralis | 0.085 (0.073-0.102) | 0.143 (0.115-0.245) |
| P. trichosuri | 0.105 (0.084-0.133) | 0.297 (0.214-0.515) |
| A. caninum | 0.608 (0.429-0.765) | 1.178 (0.913-2.100) |
| H. contortus | 1.793 (1.516-2.558) | 2.765 (2.010-5.915) |

Table 9 shows a comparison of the doses (mg/ml) of eryngial and ivermectin after 48 hr that were required to kill 50% of S. stercoralis and H. contortus infective larvae. Mortality doses were not obtained for P. trichosuri and A. caninum. Using S. stercoralis infective larvae, the $LD_{50}$ of eryngial (0.069) was significantly lower than the $LD_{50}$ of ivermectin (0.306). This was also true for H. contortus infective larvae, in that the $LD_{50}$ of eryngial (1.361) was significantly lower than the $LD_{50}$ of ivermectin (4.990). Using eryngial, the 48 hr $LD_{50}$ for S. stercoralis (0.069) was significantly lower than the 48 hr $LD_{50}$ for H. contortus (1.361). A similar trend was seen using ivermectin, in that the 48 hr $LD_{50}$ for S. stercoralis (0.306) was significantly lower that the 48 hr $LD_{50}$ for H. contortus (4.990).

TABLE 9

Doses of eryngial and ivermectin required to kill 50% ($LD_{50}$) of S. stercoralis and H. contortus infective larvae respectively, after 48 hr in vitro

| Parasite | Eryngial 48 hr $LD_{50}$ (mg/ml) ± 95% confidence intervals | Ivermectin 48 hr $LD_{50}$ (mg/ml) ± 95% confidence intervals |
|---|---|---|
| S. stercoralis | 0.069 (0.058-0.085) | 0.306 (0.203-0.442) |
| H. contortus | 1.361 (1.284-1.449) | 4.990 (4.572-5.954) |

Table 10 shows 90% mortality doses (mg/ml) of eryngial and ivermectin after 48 hr for S. stercoralis and H. contortus infective larvae. For S. stercoralis L3 larvae, the $LD_{90}$ of eryngial (0.105) was significantly lower than the $LD_{90}$ of ivermectin (1.038). This was also the case for H. contortus, in which the $LD_{90}$ of eryngial (2.360) was significantly lower than the $LD_{90}$ of ivermectin (0.6.949). With eryngial, the $LD_{90}$ for S. stercoralis (0.105) was significantly lower than its $LD_{90}$ for H. contortus (2.360). This was also the case with ivermectin, in that the $LD_{90}$ for S. stercoralis (1.038) was significantly lower than its $LD_{90}$ for H. contortus (6.949). For both S. stercoralis and H. contortus L3 larvae, the $LD_{50}$ were significantly different from the corresponding $LD_{90}$, respectively.

TABLE 10

Doses of eryngial and ivermectin required to kill 90% ($LD_{90}$) of Strongyloides stercoralis and Haemonchus contortus infective larvae respectively, after 48 hr in vitro

| Parasite | Eryngial 48 hr $LD_{90}$ (mg/ml) ± 95% confidence intervals | Ivermectin 48 hr $LD_{90}$ (mg/ml) ± 95% confidence intervals |
|---|---|---|
| S. stercoralis | 0.105 (0.085-0.174) | 1.038 (0.665-2.498) |
| H. contortus | 2.360 (2.109-2.768) | 6.949 (5.858-10.10) |

A comparison of the 48 hr $LD_{50}$ (0.069) and $LD_{90}$ (0.105) of eryngial against *S. stercoralis* L3 larvae indicated no significant difference between these values (Tables 9 and 10). However, for *H. contortus* infective larvae using eryngial, the 48 hr $LD_{50}$ (1.361) was significantly lower than the 48 hr $LD_{90}$ (2.360). For ivermectin, there was a significant difference between the $LD_{50}$ (0.306) and $LD_{90}$ (1.038) against *S. stercoralis* L3 larvae. There was no significant difference however, between the $LD_{50}$ (4.990) and $LD_{90}$ (6.949) for ivermectin against *H. contortus* L3 larvae (Tables 9 and 10).

4. Discussion

The dose-dependent immobilization and mortality results of the present in vitro study confirmed eryngial's anthelmintic activity using *S. stercoralis* infective larvae and demonstrated its potential as a broad-spectrum antiworm plant compound. In all instances, the infective larvae of *P. trichosuri, S. stercoralis, H. contortus* and *A. caninum* were both immobilized and killed by eryngial. This ability to inactivate a range of parasitic nematodes typifies the effects of broad-spectrum anthelmintics. For example, methyl 5(6)-butyl-2-benzimidazolecarbamate (compound 90), which has been identified as a potent anthelmintic agent, is effective against *A. ceylanicum* (hamsters and dogs), *Hymenolepsis nana* (rats), *Nippostrongylus brasiliensis* (rats), *Syphacia obvelata* (mice), *A. tubaeformis* (cat), *Toxocara* species (cat) and *Litomosoides carinii* (cotton rat) (Kumar, S. et al., *Journal of Medical Chemistry,* 27(8): 1083-1089, 1984). A study by Ostlind et al. (*Journal of Helminthology,* 80:393-396, 2007) indicated three benzimidazoles: thiabendazole, oxfendazole and albendazole; a tetrahydropyrimidine: morantel; an imidazothiazole: levamisole hydrochloride; a macrocyclic lactone: ivermectin; and an experimental natural product, paraherquamide, to be active against various stages of the parasitic nematodes *Trichostrongylus colubriformis, T. sigmodontis* and *H. contortus.* Tribendimidine, a promising, safe and broad-spectrum anthelmintic agent, showed high efficacy against *N. braziliensis* (rats), *Necator americanus* (hamsters), *A. caninum, T canis* (dogs) and *Syphacia mesocriceti* (mice) in laboratory studies (Shy-Hua, X. et al., *Acta Tropica,* 94(1):1-14, 2005). In this study, based on the 24 hr doses required to immobilize the infective larvae, *P. trichosuri* was most sensitive to the anthelmintic effect of eryngial. There was a 10.2 and 41.9 fold statistically significant ($p<0.05$) increase in the dose required to immobilize a similar percentage (50%) of *H. contortus* and *A. caninum*, respectively. Though less sensitive to eryngial than *P. trichosuri* by 4.5 fold, *S. stercoralis* was noticeably more sensitive to the plant compound than *H. contortus* and *A. caninum*, showing a comparative significant decrease of 2.3 and 9.4 fold, respectively, in the 50% immobilization dose. A significantly more potent dose of eryngial was also required to immobilize 90% of the infective larvae of each parasite. However, the increased sensitivity of *P. trichosuri* to eryngial when compared to *A. caninum* was a 9.4 fold difference. The increased sensitivity to eryngial by *P. trichosuri* over *H. contortus* (8.5 fold) and *S. stercoralis* over *A. caninum* (10.7 fold) were similar to the trend depicted by the 24 hr $ID_{50}$ doses.

A similar trend was seen for mortality of the infective larvae. Using 24 hr 50% mortality doses, *S. stercoralis* showed a statistically significant ($p<0.05$) 7.2 and 21.1 fold increase in sensitivity to eryngial than *A. caninum* and *H. contortus*, respectively. *P. trichosuri* demonstrated a 5.8 and 17.1 fold increase in sensitivity over these two parasites. Also, except for *H. contortus*, a significantly more potent dose of eryngial was required to kill 90% of the larvae than the 50% mortality doses. Increased sensitivity to eryngial by *S. stercoralis* over *A. caninum* (8.2 fold) and *H. contortus* (19.3); and by *P. trichosuri* over *A. caninum* (4 fold) and *H. contortus* (9.3 fold), respectively, were similar to the trend indicated by the 24 hr $LD_{50}$ doses.

A comparison of the 48 hr $ID_{50}$ values using *S. stercoralis* infective larvae showed eryngial to be 2.5 times more potent than ivermectin. However, ivermectin was 28.5 times more effective than eryngial at immobilizing *H. contortus* infective larvae. The 48 hr $ID_{90}$ values also indicated that eryngial was 3.9 times more effective than ivermectin using *S. stercoralis* L3 larvae, while ivermectin was 12.9 times greater in potency than eryngial using *H. contortus* infective larvae. The 48 hr $LD_{50}$ of eryngial (0.069 mg/ml) was 4.4 times more effective than ivermectin against *S. stercoralis*. The 48 hr $LD_{90}$ of eryngial (0.105 mg/ml) was even more potent, being 9.9 times more potent than ivermectin using *S. stercoralis*. Unlike the immobilization dose response, eryngial was 3.7 times more potent at killing 50% of *H. contortus* infective larvae than ivermectin, and was 2.9 times more effective than ivermectin at eliciting 90% mortality.

The results of this study for eryngial and ivermectin confirm previous findings by Forbes et al. (unpublished). Based on the time (hr) taken to kill 50% ($LT_{50}$) of *S. stercoralis* L3 larvae, eryngial was significantly more potent than ivermectin, recording a 7.1 fold increase in effectiveness after 120 hr of incubation. Eryngial, therefore, is a more potent agent than ivermectin in vitro, a drug well established as having broad-spectrum activity against a range of parasitic infections. Although the recommended dose of ivermectin for treating *S. stercoralis* infections in humans is 150-200 μg/kg (0.15-0.2 mg/kg) and is based on in vivo studies, the favorable results obtained here for eryngial points to its efficacy as a new agent for drug development. Studies already have established ivermectin as a much more effective anthelmintic than thiabendazole and albendazole for treating *S. stercoralis* infections.

Eryngial's potential effectiveness also is demonstrated when a comparison is made between the findings of Wang et al. (1989) and the present study. Wang et al. conducted an in vitro investigation on the efficacy of ivermectin using various life-cycle stages of *A. canimun*. Doses of 2.5 and 560 mg/ml of ivermectin killed L3 larvae and adult worms, while a dose of 1000 mg/ml was detrimental to eggs inside the uterine tissue of female worms. The 24 h 50% and 90% mortality doses of eryngial against *A. caninum* infective larvae were 1.793 and 2.765 mg/ml, respectively. An in vivo study demonstrated ivermectin's effectiveness in clearing the infection completely from infected dogs.

The potential effectiveness of eryngial for treating yet another parasitic nematode, *P. trichosuri*, is shown by a comparison of the results of this study with that of Ralston et al. (2001). Their in vivo investigation showed that a dose of doramectin (0.6 mg/kg) reduced *P. trichosuri* infection in possums by 99% ($p<0.05$). The in vitro mortality dose of eryngial (0.297 mg/ml) against *P. trichosuri* supports its efficacy as a broad-spectrum anthelmintic drug.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of inhibiting the growth of or killing a parasite of the genus *Trypanosoma*, comprising administering to a mammal infected with said parasite a therapeutically effective amount of trans-2-dodecenal.

2. The method according to claim 1, wherein said therapeutically effective amount is in a unit dosage form.

3. The method according to claim 1, wherein said mammal is a human.

4. The method according to claim 1, wherein said *Trypanosoma* parasite is selected from the group consisting of *Trypanosoma rangeli, Trypanosoma mega, Trypanosoma avium, Trypanosoma conorhini, Trypanosoma brucei gambiense, Trypanosoma brucei rhodesiense* and *Trypanosoma cruzi*.

5. The method according to claim 1, wherein said trans-2-dodecenal is isolated from plant sources selected from the group consisting of *Eryngium foetidum* and *Coriandrum sativum*.

6. The method according to claim 1, wherein the route of administration of the trans-2-dodecenal is selected from the group consisting of oral, parenteral and topical.

7. The method according to claim 6, wherein said route of administration is a parenteral route selected from the group consisting of intravenous, intramuscular and subcutaneous.

8. The method according to claim 6, wherein oral administration is in the form of hard or soft shell gelatin capsules, tablets or lozenges.

\* \* \* \* \*